US00PP20363P2

(12) United States Plant Patent
Chandler

(10) Patent No.: US PP20,363 P2
(45) Date of Patent: Sep. 29, 2009

(54) STRAWBERRY PLANT NAMED 'FLORIDA RADIANCE'

(50) Latin Name: *Fragaria×ananassa*
Varietal Denomination: Florida Radiance

(75) Inventor: Craig Chandler, Tampa, FL (US)

(73) Assignee: University of Florida Board of Trustees, Gainesville, FL (US)

( * ) Notice: Subject to any disclaimer, the term of this patent is extended or adjusted under 35 U.S.C. 154(b) by 0 days.

(21) Appl. No.: 12/151,407

(22) Filed: May 7, 2008

(51) Int. Cl.
*A01H 5/00* (2006.01)

(52) U.S. Cl. ..... Plt./208

(58) Field of Classification Search ..... Plt./208
See application file for complete search history.

*Primary Examiner*—Annette H Para

(57) ABSTRACT

A new and distinct variety of strawberry (*Fragaria×ananassa*), which originated from seed produced by a hand-pollinated cross between 'Winter Dawn' and FL 99-35. The new strawberry, named 'Florida Radiance', is distinguished by high December through March production of fruit that are large, firm, glossy, and resistant to anthracnose fruit rot when grown in west central Florida or other areas that have a subtropical climate similar to that of west central Florida.

2 Drawing Sheets

Botanical designation: *Fragaria×ananassa* Duchesne.

BACKGROUND OF THE NEW VARIETY

The present invention relates to a new and distinct variety of strawberry (*Fragaria×ananassa* Duchesne) plant that is named 'Florida Radiance' and more particularly to a strawberry plant that is distinguished by its high fruit yield during the winter in west central Florida, as well as its ability to produce large, glossy fruit that are resistant to infection by *Colletotrichum acutatum*. Asexual propagation was performed at Dover, Fla. where the selection was made and plants were tested. Contrast is made to 'Strawberry Festival' (U.S. Plant Pat. No. 14,739), currently the dominant variety in Hillsborough County, Fla., for reliable description. This new variety is a promising candidate for commercial success because it produces high yields of firm, attractive fruit during a desirable market window.

ORIGIN OF THE VARIETY

This strawberry plant (genotype) originated in a strawberry breeding plot at Dover, Fla. The seed parent was 'Winter Dawn' (U.S. patent application Ser. No. 11/093,191), a strawberry variety with high early-season yield potential and ability to produce large primary and secondary fruit. The pollen parent was FL 99-35 (not patented), a University of Florida breeding selection with the ability to produce firm, attractive fruit. The seeds resulting from the controlled hybridization were germinated in a greenhouse and the resulting seedlings were planted and allowed to produce daughter plants by asexual propagation (i.e. by runners). Two daughter plants from each seedling were transplanted to raised beds, where they fruited. 'Florida Radiance' strawberry (as represented by two daughter plants from the original seedling) exhibited attractive fruit, and therefore was selected for further evaluation. 'Florida Radiance' was the 116th selection numbered in the 2001–02 stage 1 trial, and thus was designated FL 01-116. It has been asexually propagated by runners, annually, and further test plantings have established that the vegetative and fruit characteristics of the propagules are identical to the initial two daughter plants.

SUMMARY OF THE VARETY

'Florida Radiance', when grown in a subtropical fall and winter climate, is set apart from all other strawberry plants by a combination of the following characteristics: ability to produced high yields of large, firm, glossy fruit throughout the main production period; ease of harvest; and resistance to anthracnose fruit rot.

BRIEF DESCRIPTION OF THE DRAWING

The accompanying photographs show a typical specimen of the plant and fruit as seen in early March in west central Florida.

DETAILED BOTANICAL DESCRIPTION

The following botanical description is that of mature plants of the variety grown under the ecological conditions (warm days, cool nights) prevailing at Balm, Fla. in March. Colors are described using a standard Royal Horticultural Society (R.H.S.) Color Chart.

'Florida Radiance' is a short day cultivar. Average height and width for mature plants is 21 cm and 29 cm respectively. Average petiole length and diameter is 15.5 cm and 2.8 mm respectively, and petioles have a light to medium pubescence. Average length and breadth of terminal leaflets is 66 and 58 mm respectively. Average length and breadth of secondary leaflets is 54 and 48 mm respectively. Leaflet margins are crenate and average 20 serrations per terminal leaflet, and 17 per secondary leaflet. The upper leaf surface is a dark grey green (RHS 139B); the lower leaf surface is a light grey green (RHS 139C); and the petiole is a medium yellow green (RHS 145A). Flowers open below the canopy, and have 6 to 8 petals and an average of 26 stamens. Individual petals have a length of 12 mm and a width of 10 mm. The diameter of the corolla (i.e. the petals collectively) is 32 mm. The color of the calyx is yellow green (RHS 141B). Pedicels attached to mature primary fruit are 10.8 to 12.0 cm long, with branching of the inflorescence usually occurring very close to the crown. At peak production, the plant will have 3 to 4 crowns, each producing a truss, and each truss will have three to seven pedicels. Mean fruit weight is greater than that of 'Strawberry Festival' (Table 1 and 2). Primary fruit are mostly medium conic in shape (weighing 30–40 g), with some being asymmetrical, and some early season fruit being elongated; whereas secondary and tertiary fruit are mostly short to medium conic (weighing 10–30 g). Occasionally, a primary fruit of 'Florida Radiance' will have a small hollow cavity at its center, but a cavity in a secondary and tertiary fruit of this cultivar is rarely, if ever, seen. The achenes are slightly sunken, giving the fruit a smooth appearance. External fruit color is a glossy bright (RHS 34B) to dark red (RHS 181A) (depending on maturity). 'Florida Radiance' fruit are not significantly different in lightness than 'Strawberry Festival' fruit (Table 3). The internal color of 'Florida Radiance' fruit is a warm red (RHS 34A). The calyx is generally medium to large in size and attractive. Fruit of 'Florida Radiance' are firm (Table 3), yet juicy. We consider the flavor of the fruit to be acceptable, and good under ideal growing conditions, but it is usually not as highly regarded as fruit of 'Strawberry Festival' that has been harvested fully mature (Table 4). The preferred planting date for 'Florida Radiance' is October 5th to October 15th. Yields of 'Florida Radiance' were complementary to those of 'Strawberry Festival' during both the 2003–04 and 2004–05 seasons (Tables 1 and 2). 'Florida Radiance' had higher production than 'Strawberry Festival' in February, while 'Strawberry Festival' had higher production than 'Florida Radiance' in January. 'Florida Radiance' is resistant to one of the most serious disease problems on strawberry in Florida: anthracnose fruit rot (caused by *Colletotrichum acutatum*). In an unsprayed trial during the 2007–08 season, only 3% of the 'Florida Radiance' fruit harvested from mid February to mid March showed symptoms of anthracnose fruit rot, compared to 53% for 'Treasure' (U.S. Plant Pat. No. 12,414), the susceptible control (N. Peres, unpublished data). But 'Florida Radiance' is susceptible to crown rots (C. K. Chandler, personal observations), which are most likely caused by *C. gloeosporioides* or *Phytophthora* spp. The susceptibility of 'Florida Radiance' to the twospotted spider mite (*Tetranychus urticae* Koch) is unknown, but a serious infestation has not yet been observed in research center or commercial trials.

TABLE 1

Performance of strawberry cultivars at Dover, Fla. during the 2003-04 season.

| | Marketable yield (g/plant) | | | | | Wt/ |
|---|---|---|---|---|---|---|
| Cultivar | December | January | February | March | Total | fruit[z] (g) |
| F. Radiance | 65 a[y] | 77 b | 270 a | 435 a | 847 a | 21.2 a |
| S. Festival | 44 a | 112 a | 84 b | 642 a | 881 a | 18.5 b |

[z]Mean fruit weight was determined by dividing total marketable fruit yield per plot by total marketable fruit number per plot.
[y]Means based on four replications of 10 plants each. Mean separation within columns by Fisher's protected LSD test, P ≦ 0.05.

TABLE 2

Performance of strawberry cultivars at Dover, Fla. during the 2004-05 season.

| | Marketable yield (g/plant) | | | | | Wt/ |
|---|---|---|---|---|---|---|
| Cultivar | December | January | February | March | Total | fruit[z] (g) |
| F. Radiance | 86 a[y] | 82 b | 321 a | 558 a | 1047 a | 22.4 a |
| S. Festival | 37 b | 144 a | 155 b | 592 a | 928 b | 20.6 b |

[z]Mean fruit weight was determined by dividing total marketable fruit yield per plot by total marketable fruit number per plot.
[y]Means based on four replications of 10 plants each. Mean separation within columns by Fisher's protected LSD test, P ≦ 0.05.

TABLE 3

Physical and chemical characteristics of strawberry fruit harvested at Floral City, Fla. 12 Feb. 2008[z].

| Cultivar | Surface color L value[y] | Firmness[x] | Soluble solids (%) | Titratable acidity (% citric acid) |
|---|---|---|---|---|
| S. Radiance | 37.5 | 0.44 | 6.8 | 0.81 |
| S. Festival | 38.1 | 0.36 | 7.8 | 0.84 |

[z]L and firmness values are the average of eight observations.
[y]L value is a measure of lightness and darkness, with 0 being totally black and 100 being totally white.
[x]Firmness is expressed as kilograms of force to penetrate the fruit to a depth of 10 mm with a 5 mm diameter probe.

TABLE 4

Sensory characteristics of strawberry fruit harvested at Floral City, Fla. 12 Feb. 2008[z].

| Cultivar | Appearance | Color | Firmness | Flavor | Sweetness |
|---|---|---|---|---|---|
| F. Radiance | 6.8 a | 6.8 a | 6.6 b | 5.7 b | 5.5 b |
| S. Festival | 7.1 a | 6.9 a | 7.1 a | 6.8 a | 6.3 a |

[z]Means based on the ratings of 100 untrained panelists. Mean separation within columns by Tukey's test, P ≦ 0.05. Characteristics are rated on a 1-9 hedonic scale, with 1 = dislike extremely, 5 = neither like nor dislike, and 9 = like extremely.

I claim:

1. A new and distinct strawberry plant as illustrated and described, characterized by 1) resistance to anthracnose fruit rot, and 2) high December through March production of large, glossy fruit when grown in west central Florida.

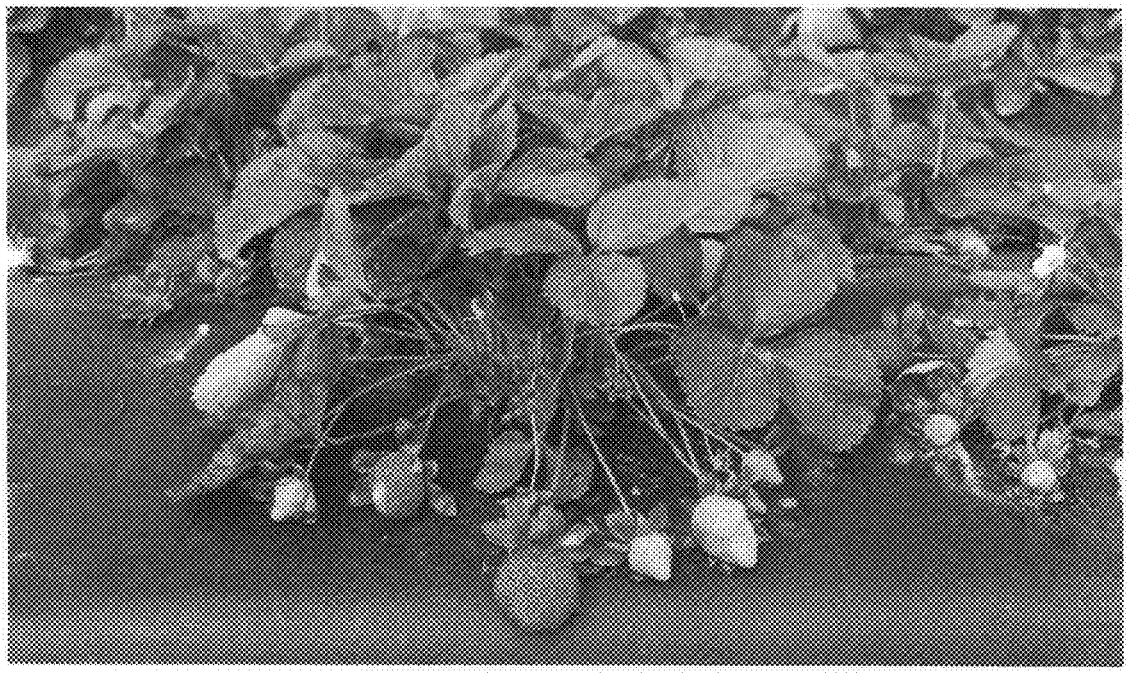

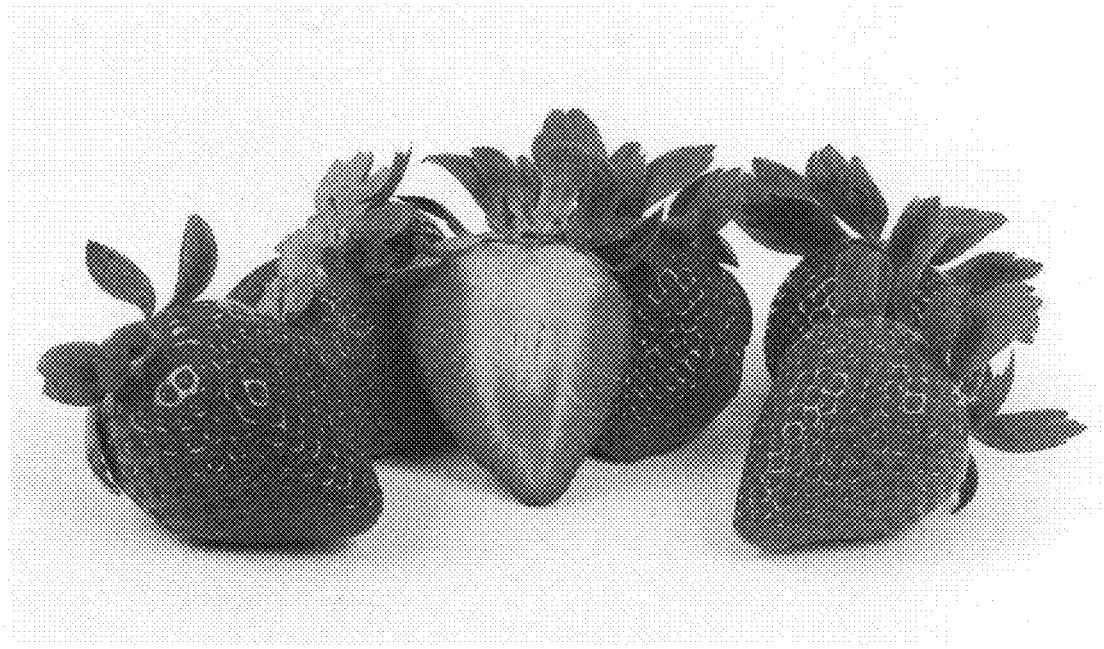

* * * * *